(12) United States Patent
Suokas et al.

(10) Patent No.: US 7,964,206 B2
(45) Date of Patent: Jun. 21, 2011

(54) POROUS MEDICAL DEVICE AND METHOD FOR ITS MANUFACTURE

(75) Inventors: Esa Suokas, Tampere (FI); Pertti Törmälä, Tampere (FI); Nureddin Ashammakhi, Tampere (FI); Heimo Ylänen, Turku (FI); Mikko Hupa, Turku (FI)

(73) Assignee: Bioretec Oy, Tampere (FI)

(*) Notice: Subject to any disclaimer, the term of this patent is extended or adjusted under 35 U.S.C. 154(b) by 1221 days.

(21) Appl. No.: 10/568,890

(22) PCT Filed: Aug. 20, 2004

(86) PCT No.: PCT/FI2004/050117
§ 371 (c)(1),
(2), (4) Date: Oct. 17, 2006

(87) PCT Pub. No.: WO2005/018698
PCT Pub. Date: Mar. 3, 2005

(65) Prior Publication Data
US 2007/0141111 A1    Jun. 21, 2007

(30) Foreign Application Priority Data
Aug. 20, 2003 (FI) ..................... 20031174

(51) Int. Cl.
*A61K 48/00* (2006.01)
*B32B 27/04* (2006.01)

(52) U.S. Cl. ............... 424/422; 424/426; 424/93.21; 442/123

(58) Field of Classification Search ............ None
See application file for complete search history.

(56) References Cited

U.S. PATENT DOCUMENTS

| | | | |
|---|---|---|---|
| 4,655,777 A | | 4/1987 | Dunn et al. |
| 4,669,474 A | * | 6/1987 | Barrows ............. 606/152 |
| 4,968,317 A | | 11/1990 | Tormala et al. |
| 4,997,446 A | | 3/1991 | Thoma |
| 5,084,051 A | * | 1/1992 | Tormala et al. ......... 606/77 |
| 5,108,755 A | | 4/1992 | Daniels et al. |
| 5,615,563 A | | 4/1997 | Matsuda et al. |
| 5,626,861 A | | 5/1997 | Laurencin et al. |
| 5,652,056 A | | 7/1997 | Pepin |
| 6,054,400 A | | 4/2000 | Brink et al. |
| 6,121,172 A | | 9/2000 | Marcolongo et al. |
| 6,406,498 B1 | | 6/2002 | Tormala et al. |
| 6,451,059 B1 | | 9/2002 | Janas et al. |
| 6,503,278 B1 | | 1/2003 | Pohjonen et al. |
| 6,579,533 B1 | | 6/2003 | Tormala et al. |
| 6,884,427 B1 | | 4/2005 | Barrows |
| 7,186,759 B2 | | 3/2007 | Seppala et al. |
| 2002/0143403 A1 | | 10/2002 | Vaidyanathan et al. |
| 2003/0050711 A1 | | 3/2003 | Laurencin et al. |
| 2004/0258732 A1 | | 12/2004 | Shikinami |

FOREIGN PATENT DOCUMENTS

| | | | |
|---|---|---|---|
| WO | WO 00/47245 | * | 2/2000 |
| WO | WO 00/47245 | | 8/2000 |
| WO | WO 02/07961 | * | 1/2002 |

OTHER PUBLICATIONS

Finnish Office Action dated Sep. 26, 2008.
STN International, "Biodegradable Three-Dimensional Knitted Fabrics for Medical Use," File CAPLUS, CAPLUS Accession No. 2003:187879, Doc. No. 138:210394, Unitica Fiber K.K.
Database WPI, Week 200375, Derwent Publication Ltd., London, GB, AN 2003-792583.

* cited by examiner

*Primary Examiner* — Robert A Wax
*Assistant Examiner* — Danah Al-Awadi
(74) *Attorney, Agent, or Firm* — Kenyon & Kenyon LLP

(57) ABSTRACT

Porous bioabsorbable, bioactive and load-bearing composite medical device structure includes a plurality of regular textile planar layers (1*a*, 1*b* . . . ) formed of continuous bioabsorbable polymer matrix and bioceramic fibers acting as reinforcements, both included in continuous fibrous elements (3) forming the textile layers. The layers are placed on top of each other to form a structure having two dimensions (x, y) at right angles to each other according to the two dimensions of the textile layer and a third dimension (z) perpendicular to them and resulting from the piling of the layers. A plurality of passages extend through the layers as a result of the openings (2) defined by portions of the continuous fibrous elements (3) extending substantially in the direction of the plane. The continuous fibrous elements (3) comprise both bioactive ceramic reinforcing fibers which form a reinforcing structure and a bioabsorbable polymer matrix material which forms a matrix which binds the layers together and also binds the portions of continuous fibers defining the openings together, thereby forming the passages and stiffening the structure. This bioactive and bioabsorbable composite structure is suitable to be used as a basic structure in medical devices, especially in osteochondral applications where the load-bearing properties of implant are required.

28 Claims, 4 Drawing Sheets

“POROUS MEDICAL DEVICE AND METHOD FOR ITS MANUFACTURE

FIELD OF THE INVENTION

The invention relates to a porous bioabsorbable, bioactive and load-bearing composite medical device structure and to a method for manufacturing a structure of this kind.

BACKGROUND OF THE INVENTION

So far, various medical composite materials have been developed to address the problem of wound healing. Man has long searched for proper materials to aid healing and regeneration of tissues or their replacement when the first option fails. Man has borrowed solutions and materials from nature. The first biomaterials used by man were derived from naturally occurring materials such as catgut that has been documented used by old Egyptians. Indians have used various replacement materials. For demanding tissues where mechanical properties are important, i.e. hard tissues for their primary function to keep the frame of the body, cartilage and bone were thus treated mainly with splinting and immobilization. However, this procedure implies the loss of function and disability that, although, temporary, it can lead to complications. When metals were used for fixing bone fractures, it was possible to make patients walk very early and resume function, and thus an "internal" splinting system was introduced. In the recent years research in the area of tissue generation and regeneration has expanded and new principle of treatment has been developed to allow for making grafts in the laboratory. For a body frame-keeping, load bearing system comparable to bone, it has been difficult to develop reliable biomaterials that are biocompatible, temporarily present in the body (elimination by body itself), and mechanically reliable. Such a material that can be used to aid bone repair, regeneration or generation and/or augmentation that can also be used to help osteoconduction is not present up to our knowledge and there is a burning need to develop such a material.

Various materials have been developed to act as scaffolds for bone tissue generation or regeneration. They have been called so because they offer a medium to which cells can attach and can be transplanted (carriers). However, early scaffolds were made of polymers, namely polyesters, polyglycolide, polyglycolide/polylactide and later from polylactide. These polymers as such may not always possess sufficient strength to bear weight and an additional supporting mechanism is needed to help bone in weight-bearing which the function of the scaffold is limited to support the healing of the void, defect or gap with bone regeneration by transplanted cells or tissue grafts such as periosteum.

On the other hand devices based on ceramics alone have also been explored back in the history as filler materials and recently as scaffolds for tissue generation, regeneration or repair. Hydroxyapatite is one example of ceramics that has been studied. However, hydroxyapatite, although biocompatible and osteoconductive, is practically not bioabsorbable and may lead to formation of fibrous tissue at the interface between the bone and the implant. Tricalcium phosphate has been found to be a resorbable ceramic that can be osteoconductive as well. With the current technology, it is however, difficult to manufacture it into fibers. Bioactive glass that can lead to formation of apatite layer at the interface between bone and the ceramic has been used as filler material in some clinical cases. With recent advances, it has been possible to make bioactive glass into fibers. However, these fibers alone are brittle and can not bear the load when used in the skeleton that should bear the weight of the body. There is, thus, an obvious need to develop a reliable, osteoconductive device for treatment of bone and/or cartilage fractures, osteotomies, defects that may follow trauma, congenital deficiencies, disease or surgical resection.

An example of a biocompatible implant is shown in U.S. Pat. No. 5,084,051. The implant is made of biocomposite material comprising at least one bioceramic component layer and at least one material component layer, which has been manufactured of at least one polymer, both components having certain porosity.

U.S. Pat. No. 6,579,533 describes a bioabsorbable drug delivery material comprising synthetic bioabsorbable polymeric matrix, antibiotic and bioactive glass dispersed in the polymeric matrix. The document mentions a possibility to spin drug releasing materials to fibers which can be formed to knitted or woven fabrics for example.

U.S. Pat. No. 5,626,861 is a good example of a conventional technique for obtaining 3-dimensional macroporous polymer matrices for use as bone graft or implant material. Mixing a polymer solution, hydroxyapatite particles and inert particles, which are removed by leaching after the solvent of the polymer has evaporated, forms the composite. The technique requires many processing steps and use of organic solvents. The inner porosity cannot be thoroughly controlled through this procedure.

Publication WO 02/08320 shows a simpler technique avoiding the use of solvents, but it still requires the use of the special "porogen" substance, which must be removed from the composition to create the porosity.

An example of a biocompatible implant for surgical implantation is shown in US published patent application no. 2002/0143403 and corresponding publication WO 02/053105. This implant comprises a matrix of a resorbable thermoplastic-ceramic composition, the matrix having a pore size and porosity effective for enhancing bone growth adjacent the composition. The implant structure is made by using ribbon or filament deposition process. The ribbons or filaments of extruded composition are deposited layer upon layer onto the work or support surface in a predetermined pattern to form an object of desired size and shape and having the desired porosity characteristics, using a special extrusion freeform (EFF) process. One material for the composition is a blend of thermoplastic polymer and calcium phosphate.

SUMMARY OF THE INVENTION

The purpose of the invention is to provide a medical device of controlled porosity without the use of a special "porogen" removing step or special filament deposition process in its manufacture.

A porous, mechanically reliable, biocompatible, bioabsorbable, bioactive composite medical device is made to achieve successful hard tissue (cartilage tissue and/or bone) generation, regeneration, repair or augmentation. The composite structure is composed in a special multilayered fashion of a plurality of individual textile layers having openings to constitute a matrix made of bioabsorbable biopolymer fibers or filaments, reinforced with bioactive ceramic elements, especially fibers. The structure provided by the textile layers comprises interconnecting channels and pores to provide a suitable environment and scaffold for in vitro cell seeding and extracellular matrix synthesis and/or in vivo integration into body tissues upon implantation (including in vitro stage or used for in situ tissue engineering, tissue repair, support, fixation or tissue augmentation). The composite medical device of the current invention has reliable mechanical strength to be effective for use in the management of hard tissues such as bone, cartilage and their composites in the above-mentioned applications. Accordingly, tissue construction, reconstruction or repair can be achieved by using the device of the current invention involving in vitro cell culture stage, then implanting the structure into in vivo environment, or it can be be directly implanted into in vivo environment in the mammalian, especially human body to achieve the purposes of use listed above. It can be used to carry cells (genetically modified or non-modified), and/or other agents such as cytokines, pharmacological agents, or genes (using viral or nonviral vectors), or even useful micro-organisms, to help its ultimate function in achieving the purposes listed above. After the function of generation, regeneration, repair or augmentation of treated tissue or tissue defect is achieved the device is absorbed and no foreign body is left behind where the device material is completely replaced by native tissues.

The thickness of the device can be varied by selecting the number of textile layers to be piled. The porosity can be controlled by choosing the size of the openings (mesh size) in the layers. The porosity in the direction of thickness of the device can also be varied by varying the size or form of the openings or the textile type in the same structure. If the device of constant thickness is not desired on the final implantation site, the device can be made into the 3-dimensional shape fitting to the body by piling layers of selected shape one on top of the other and stiffening the structure, or by molding an entity of piled layers to the final stiffened shape.

It is of advantage, when textiles of regular structure is used, these forming a certain pattern formed of interlaced fibrous elements and ensuring for their part an even pore distribution or a controlled variation of the pore distribution in the final structure.

The pores have the well-known advantage of affording a site of tissue growth and channels for transfer of matter, but they can be also used for incorporating various substances and cells that can not be embedded in the matrix polymer.

DETAILED DESCRIPTION OF THE INVENTION

Terminology

Figure 1:
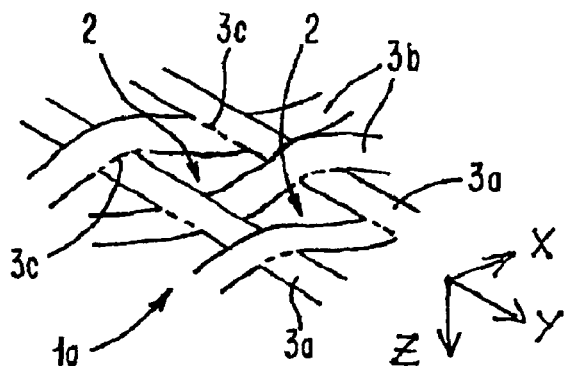
FIG. 1 shows a detail of the structure according to the invention having woven fabric as the substructure.

The composite comprises bioabsorbable matrix material, e.g. plastics, and reinforcing elements in the form of bioactive ceramic elements.

The term "fiber" used in this specification is meant to describe continuous filament and staple fiber (discontinuous fiber of limited length, typically under 10 mm).

The term "fibrous element", used for the basic constituent of the textile layer, refers to an elongate flexible element that can be mechanically made into a two-dimensional textile structure but not necessarily constituted of individual fibers.

The term "ceramic" refers to any material of non-metal and inorganic origin (definition agreed on at concensus conferences on biomaterials).

The term "biomaterial" refers to material intended to have an interface with biological systems and that is used to evaluate, treat, augment or replace any tissue, organ or function of the body (definition agreed on at concensus conferences on biomaterials).

The term "bioactive" refers to bioactive materials designed to elicit or modulate biological activity (definition agreed on at concensus conferences on biomaterials).

General Mechanical Requirements

In the discussion under this heading, the requirements of a bioabsorbable composite from purely mechanical and materials technology point of view are dealt with. From this discussion, the structural advantages and manufacturing advantages will be apparent. The medical behaviour of the components of the composite structure will be discussed in later sections.

As to the reinforcement structure, a composite can be based on continuous or staple fibers. The staple fibers can be divided by length into short ones, i.e., fibers under 1 mm and those in the range of 1-3 mm, and long ones, i.e. about 3-10 mm. In structural composites containing continuous fibers, bearing a static and dynamic load, four basic factors are to be taken into account:

the fibers, the matrix, the ordering degree and orientation of the fibers, and the bonds between the fibers and the matrix.

The bioabsorbable reinforcing fibers receiving the load determine the strength and rigidity of the structural composite. They also toughen the material by absorbing brittling energy, for example by a gliding mechanism between the binding surfaces. The bioabsorbable matrix protects and supports the reinforcing fibers, particularly in a pressing situation, as well as transmits the force on the piece from one fiber to another. In a situation of overloading, the matrix must be capable of transmitting the force between the broken filaments by means of shear between the material layers, so that the fibers could bear a traction load again. For this purpose, the fiber length must exceed a critical value. The quality of the composite is determined by how evenly the fibers are distributed in the structure and how well the bioabsorbable matrix moistens them. The latter feature is essentially dependent on the fluidity, that is, the viscosity, of the matrix.

The excellent mechanical properties of the structural composites are due to the continuous fibers, or filaments, which may be 50 times stronger and 20 to 150 times more rigid than the matrix materials. Fibers with low density (1.44-2.70 g/cm3) have high tensile strength and elastic modulus (3.0-4.5 GPa and 10-550 GPa, respectively), whereas the corresponding typical values for matrix polymers are 30-130 MPa and 2.0-4.0 GPa, respectively. During formation of the fibers, the strength of the material increases with the rise of the axial orientation of the crystals and with the decrease of defects (such as cracks and dislocations) in the microstructure. One-dimensional continuous-fiber composites are therefore much stronger in the longitudinal than in the transverse direction. It is an anisotropic material whose properties depend on the direction. The composite can thus be dimensioned according to the prevalent loading situation with a minimum material waste.

The properties of the composite are anisotropic, which is clearest in uniaxial structures. They give maximum tensile strength and modulus. As a three-dimensional stress field usually loads pieces, the one-dimensional plates must be laminated on top of each other in order to achieve reinforcement in several directions. When the continuous fibers are oriented multiaxially in a plane, pseudoisotropic laminates are obtained. In three-dimensional basic coordinates, their stiffness in the xy-plane is comparable to that of aluminum mixtures, but the transverse tensile strength and elastic modulus as well as the shearing strength are low. This is due to the differences in the elastic coefficients between different layers, and, therefore, the load of the matrix varies in the direction of the thickness of the laminate (z). Thus the breaking of the structural composite is in most cases due to the gliding of layers in relation to each other.

The processing of thermoplastic composites is based on heat and pressure, so that they are considerably faster to manufacture than corresponding thermosetting plastic composites. Because thermoforming and/or pressure forming can be repeated several times, broken structures can be easily repaired. However, in the use of bioabsorbable thermoplastics as matrices for composites it is difficult to moisten densely packed continuous fibers by viscose bioabsorbable polymers. In the present invention, the thermoplastic matrix polymer can be particularly evenly distributed in the reinforcement, contrary to the conventional melt working methods.

Thermoplastic staple fiber composites are manufactured by conventional melt working methods of polymers, for example by injection moulding, so that the orientation of the reinforcements cannot be fully controlled. In injection molding, for example, the orientation of reinforcing staple fibers and polymer molecules is influenced at the filling stage of the mold by a complex flow field with both a shearing and an extending component. When the short staple fibers are fluid-impregnated with a thermoplastic in the screw of the extruder, they are broken down in the strong shearing and extending flow because of a mutual attrition. The viscosity of technical thermoplastics being 103 to 106 times higher than that of thermosetting plastics, the polymer cannot fully moisten the whole surface area of the fibers.

In the present invention, when staple fibers are used as reinforcing structure, the same close interaction between the matrix and reinforcement fibers is attained as with filaments used as reinforcement.

Bioabsorbable Matrix Material

Synthetic bioabsorbable, biocompatible polymers, which may act as suitable matrices for the bioactive ceramic elements, especially for reinforcements of bioactive glass, can include poly-α-hydroxy acids (e.g. polylactides, polycaprolactones, polyglycolides and their copolymers, such as lactic acid/glycolic acid copolymers and lactic acid/caprolactone copolymers), polyanhydrides, polyorthoesters, polydioxanone, segmented block copolymers of polyethylene glycol and polybutylene terephtalate (Polyactive™), poly(trimethylenecarbonate)copolymers, tyrosine derivative polymers, such as tyrosine-derived polycarbonates, or poly(ester-amides). Suitable bioabsorbable polymers to be used in manufacturing of implants of the present invention are mentioned e.g. in U.S. Pat. Nos. 4,968,317, 5,618,563, FI Patent No. 98136, FI Patent No. 100217B, and in "Biomedical Polymers" edited by S. W. Shalaby, Carl Hanser Verlag, Munich, Vienna, N.Y., 1994 and in many references cited in the above publications.

The bioabsorbable matrix shall be understood to mean also a matrix comprising a blend of two or several different bioabsorbable polymers that differ from each other physically and/or in chemical structure.

Bioactive Ceramic Elements

A subgroup of bioactive ceramics comprises bioactive glasses. They are surface-active silica-based synthetic biomaterials forming a direct chemical bonding with host tissue i.e., bone. They have the ability to form a calcium phosphate layer on their surface in vivo.

Bioactive glasses have many potential clinical applications. For example, bioactive glass crush can be used as a filler material in bone defects in orthopaedics and in dentistry.

For technically more demanding applications of bioactive glass, i.e., spinning of fibers of bioactive glass, the old generation glasses can not be used due to crystallization of the amorphous material during the spinning procedure which has to be performed at high temperature.

The introduction of a newer generation of bioactive glasses enables the manufacturing of thin bioactive glass fibers. Bioactive glass fibers can be used as a component in a composite consisting of bioabsorbable polymer fibers and bioactive glass fibers. In the composite, bioactive glass functions as a tissue conductive (for example osteoconductive or chondroconductive) material, i.e., for fixation of the implant to host tissue. By changing the oxide composition of the glass, the bioactivity of the material can be controlled enabling a tailor-made fixation of the implant to different locations with different tissues and varying physical conditions. Fibrous bioactive glass can be used either as filament or staple fiber.

In another alternative, the bioactive glass can be dispersed in form of particles in the matrix material. In this alternative, bioactive glass without fiber-forming properties can also be used.

Making fibers of bioactive glass is described e.g. in U.S. Pat. Nos. 6,406,498 and 6,054,400.

In addition to or instead of bioactive glass in fibrous or particulate form, the matrix can contain calcium phosphates (CPs) in particulate form, which may act as reinforcements. The calcium phosphate can be osteoconductive, such as tricalcium phosphate and/or hydroxyapatite. Calcium phosphates (CPs) can be generally classified into two categories, the ones that are obtained by high temperature processes and the ones that can be obtained through basic solution chemistry at ambient temperatures. The high temperature CPs are those that can form $CaO-P_2O_5-H_2O$ system at temperatures beyond 500° C. The examples are monocalcium phosphate alfa- and beta-calcium phosphate, hydroxyapatite, biphasic calcium phosphate, tetracalcium phosphate and calcium pyrophosphate. A Ca/P ratio varies between 1.0 and 1.67.

Fibers based on CPs are are also included in the present invention. For example, hydroxyapatite can exist also in fibrous form, as taught by U.S. Pat. No. 5,652,056. It can be either as filament or staple fiber, and it can constitute the fibrous bioactive ceramic reinforcing structure. Also tricalcium phosphate fibers can be used, the forming of β-tricalcium phosphate fibers being described e.g. in U.S. Pat. No. 4,655,777.

Combinations

Combining the favorable properties of the bioactive ceramics and those of the thermoplastic polymers is possible with the method disclosed in this invention, where the matrix of the device is made of polymer or polymer blend and the bioactive ceramic fibers are embedded within the matrix. With the manufacturing methods applied in the current invention, it is possible to solve the challenge of having yet a porous structure with interconnected pores or channels. Although these pores may decrease the mechanical properties as compared to solid implant, the presence of reinforcing elements, preferably fibers, and the structure built thereof compensate very much for the strength drop, and the implant produced can be reliable for treatment of tissue defects in load-bearing areas such as those occuring in the bone or cartilage or both of them or osteochondral defects. The device can thus provide mechanical support, structural porosity that can home cells, and osteoconductivity and resorbability over time which makes it unique of its type.

The medical device may further contain other active agents, such as osteoinductive or antiosteolytic agents, for example embedded in the matrix polymer or in the network of interconnecting pores or channels.

Structure in Detail

The basic structural element of the structure is a continuous fibrous element. The fibrous element comprises matrix and reinforcing structure (reinforcement) in said matrix. With both the matrix and the reinforcement being fibrous, it is possible to use them for making yarns for the textile structure (co- and intermingling). If filaments are used, they can be multiplied, doubled, or double-doubled. A multiplied yarn is composed of two or more filaments, both the matrix filament and the reinforcement filament being commingled without a twist. A doubled yarn is made by twining together two or more filaments. Two doubled yarns are further combined to form a double-doubled structure.

Apart from filaments, staple fibers can also be used. Intermingling the matrix and reinforcing material units in the staple fiber form during spinning gives a more homogenous yarn than twisting them together as filaments.

Whatever the yarn forming technique is, it is of advantage if part of the reinforcement material (bioactive ceramics such as bioactive glass) is present on the surface of the yarn, which in the final structure of the device it will mean that the ceramic will be exposed in the pores, which enhances the interaction of the bioactive ceramic component with its environment, through the pores also with the outside of the medical device. One advantageous structure of the yarn for this purpose is a yarn containing bioactive ceramic staple fibers whose ends, owing to the stiffness of the fibers, spread sideways from the main running direction of the yarn in a "hairy" fashion, thus penetrating into the pores and channels inside the structure.

In the method according to the invention, the starting materials can, apart from the hybrid yarns consisting of matrix and reinforcing fibers, be flexible melt, powder or solution impregnated reinforcing fibers. The melt impregnated reinforcing fibers are manufactured by a cable covering technique by feeding the reinforcing multifilaments of bioactive ceramics through a crosshead die, wherein the melted bioabsorbable polymer forms a coating on their surface. The powder impregnated reinforcement fibers are made by driving the reinforcements through powderized bioabsorbable polymer particles which stick to the moving fibers, for example by static electricity. The path is next directed to a heated oven where the matrix polymer is melted on the surface of the fiber. Powder impregnated fibers can also be coated in a crosshead die by a melted bioabsorbable plastics that forms a coating protecting the loose particles when cooled. In all the cases above, the process step of using melted plastics can be replaced by a possible corresponding solution of a bioabsorbable polymer (solution impregnation).

Any of the above-mentioned flexible hybrid yarns formed by a thermoplastic matrix and a reinforcement that can be knitted, woven, braided or processed by another textile manufacturing method into a product with a wide surface area can be used to manufacture a light, strong and stiff composite structure with a regular porosity. By laminating the layers on top of each other, they can further be pressed by heat and pressure into a porous cellular plate. Instead of overpressure, vacuum or underpressure can be used, or the softened plate can be left to bend by gravitation according to the outlines of the mold. The obtained thermoplastic composite structure can thus be easily formed into complex geometrical surfaces.

By the method according to the invention, the thermoplastic bioabsorbable polymer matrix can be particularly evenly distributed in the reinforcement, which is not possible with the conventional melt working methods, such as injection molding, with the additional advantage that controlled porosity can be created inside the structure. Using a thermoplastic bioabsorbable polymer matrix, the reinforcements can be locked in optimal locations and positions as far as the strength calculations are concerned, with regard to the influencing stress field, as well as in shapes of high geometric complexity, an important advantage in medical implants. The invention makes possible the manufacture of pieces with very large internal surfaces and high complexity. The term "thermoplastic bioabsorbable polymer matrix" includes also blends of two or several thermoplastic bioabsorbable polymers.

Figure 2:
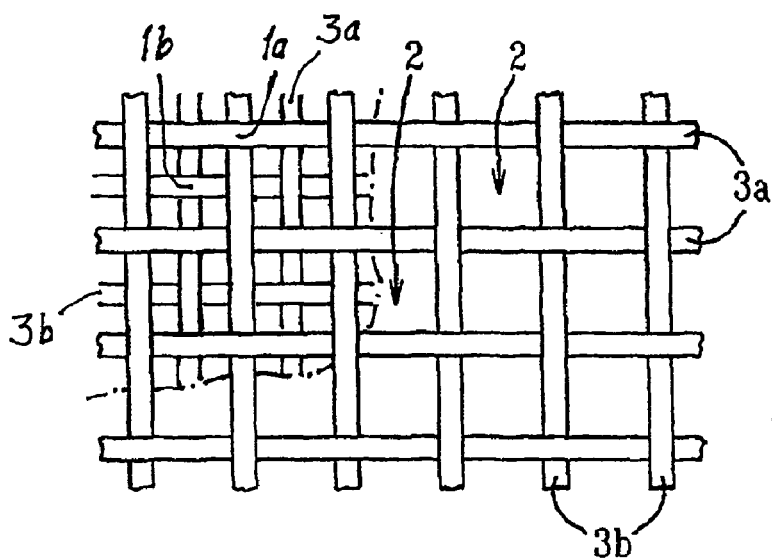
FIG. 2 shows the structure of FIG. 1 in top plan view.

FIG. 1 shows a structure of a woven fabric or a braid. The openings 2 between the weft and warp yarns or between the crossing braided yarns form quadratic or skew openings in the final product. Hybrid yarns 3 (containing both the reinforcing bioactive ceramic and the bioabsorbable polymer), serving as the weft and warp yarns or as the braided yarns, and forming the yarn sections surrounding the single openings, are merged to each other by the bioabsorbable polymer matrix in point 3c. Different layers having the two-dimensional structure as shown in FIG. 1 piled on top of each other are likewise joined by the bioabsorbable polymer matrix. FIG. 2 shows a structure according to FIG. 1 in the z-direction, in other words, in the direction perpendicular to the plane of the textile layers. As can be seen, the openings formed by the weft and warp yarns in two adjacent layers are so positioned that the crossing point of yarns 3a, 3b in one layer 1a is in the middle of the opening of the other layer, thus forming smaller openings in the direction perpendicular to the two dimensions of the individual fabrics. The purpose of the figure is to illustrate the partial overlap of the openings 2 of the different layers. The openings are more or less shifted with respect to each other when the fabrics are randomly piled.

Figure 3:
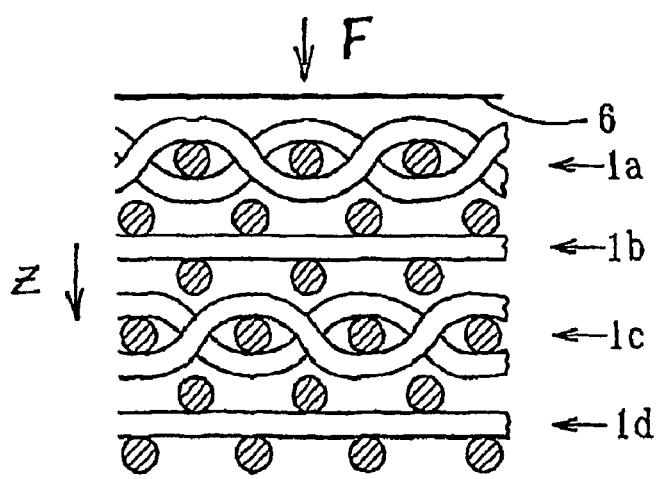
FIG. 3 shows the structure of FIG. 2 in cross-section.

FIG. 3 shows the arrangement during the manufacturing stage, where fabric layers 1a, 1b, 1c and 1d are piled on top of each other so that the weft and warp yarns 3a, 3b run in crosswise directions in the layers on top of each other. The structure according to FIG. 3 is submitted to force in the direction of the arrow F, that is in the direction perpendicular to the plane of the textile layers. With this force, the textile layers are brought closer to each other. By the simultaneous application of heat, the matrix material is melted into a continuous matrix phase in the direction perpendicular to the plane of the product. The matrix thus directly binds together the layers 1a, 1b, 1c and 1d lying on top of each other. At the same time, the weft yarns 3b and warp yarns 3a are joined together by the matrix at points 3c in FIG. 1.

Thanks to the gaps remaining between the separate woven fabric layers 1a, 1b, which is due to the wave-like course of at least some yarns along the plane of the textile layer and resulting surface irregularities of the textile layer, the structure has porosity in the direction of the plane of the textile layers as well.

The weft yarns 3a and the warp yarns 3b can also be arranged so that one of them consists solely of bioabsorbable polymer matrix material and the other of reinforcing bioactive ceramic fibers. Thus it is advantageous to pile the fabric layers on top of each other so that the reinforcing yarns are positioned in different directions in different layers, following the example of FIG. 3 (also illustrated in FIG. 2). This is advantageous for achieving isotropicity also in the case where both the weft and warp yarns of the fabrics consist of hybrid yarn. Furthermore, as one of the yarns of the woven structure consists of bioactive ceramic fiber, its contact with the environment inside the medical implant device is further enhanced, because it is well exposed in the pores.

Figure 4:
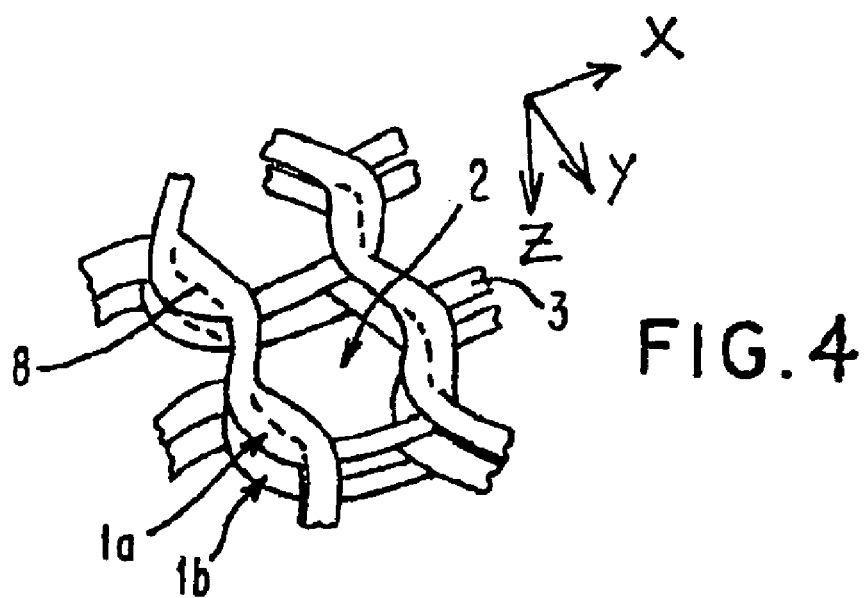
FIG. 4 shows a detail of the structure according to another embodiment, having knitted fabric as the substructure.

FIG. 4 shows a detail of the final structure according to another embodiment. The textile layers are structures knitted of a hybrid yarn 3. The openings 2 are formed by the loops of the knit. At the heat pressing stage, the fabric layers have been submitted to so high a normal force (direction z) that the fabric is extended in the planar direction (plane xy, x and y being coordinates at right angles to each other and the direction z). As a result, the loops of the fabric are opened to make a net structure, which makes at the same time the internal structure of the interconnections pores. Thus, the loops 2 of the knitted fabric have been extended during pressing into shape resembling a polygon. The point at which the matrix of the hybrid yarn 3 has bound the different adjacent yarn sections surrounding single loops is denoted by the reference numeral 8. Thanks to the gaps remaining between the separate knitted fabric layers 1a, 1b, which is due to the wave-like course of the yarns along the plane of the textile layer, the structure has porosity in the direction of the plane of the textile layers as well. This porosity can be adjusted by pressure during the manufacturing stage. Even though the openings 2 of different layers are shown aligned in FIG. 4, the different knitted layers 1a, 1b are usually piled randomly so that there is a partial overlap of the openings in the layers placed one on top of the other.

Furthermore, it is possible to use a braid as an initial structure, in which case the structure may be formed of one or several braided layers analogically to a woven fabric.

Its is also possible to have a commingled layered structure with respect to the textile layers, i.e. alternating textile layers of bioabsorbable polymer matrix material on one hand and bioactive ceramic material of the other hand. When textile layers constituted of bioabsorbable polymer matrix yarns and textile layers constituted of bioactive ceramic yarns are placed one on top of the other, the porous structure is achieved, with the bioceramic material exposed in the pores in large proportion. The matrix textile layers connect the interposed reinforcing bioceramic textile layers together to a cohesive reinforced structure. The matrix polymer does not necessarrily form continuous phase in the z direction. For example the woven layers may comprise layers where the weft and warp yarns are made of bioabsorbable polymer, without the reinforcing bioactive ceramic component, and layers where the weft and warp yarns are made of bioactive ceramic fibers, without the bioabsorbable polymer matrix component. In the above-described commingled layered textile structure, there may be several textile layers of bioabsorbable polymer matrix in contact with each other, that is, it is not necessary that every other layer is a bioactive ceramic textile layer.

Figure 5:
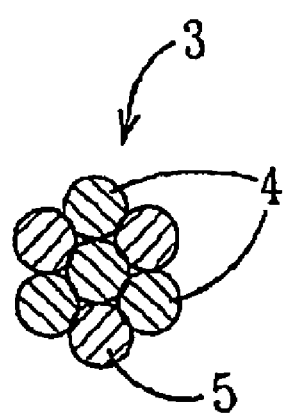
FIG. 5 shows an example of the yarn type used in the layers of the structure.
Figure 6:
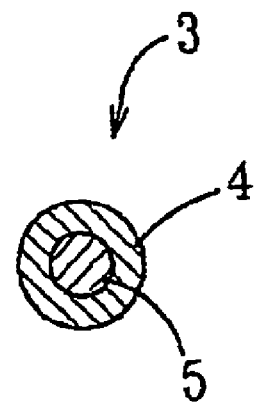
FIG. 6 shows an example of another yarn type used in the layers of the structure.

FIG. 5 shows a cross-sectional view of one type of yarn possible to be used in the textile layers 1 with openings 2. The yarn 3 is a multiplied yarn consisting of filaments 4 of bioabsorbable polymer matrix material and of filaments 5 of bioactive ceramic reinforcing material. In this type of hybrid yarn, the bioactive ceramic material will be at least partly exposed in the pores. FIG. 6, in turn, shows a continuous bioactive ceramic reinforcing filament 5 as the core of a yarn 3, covered by a continuous layer 4 of bioabsorbable polymer matrix material, which can be made by any above-described yarn forming process suitable for this yarn type. In this structure, the bioactive ceramic component will be gradually exposed as the polymer component is gradually absorbed when the medical device of the present invention is implanted in a living tissue environment of the mammalian body.

Figure 7:
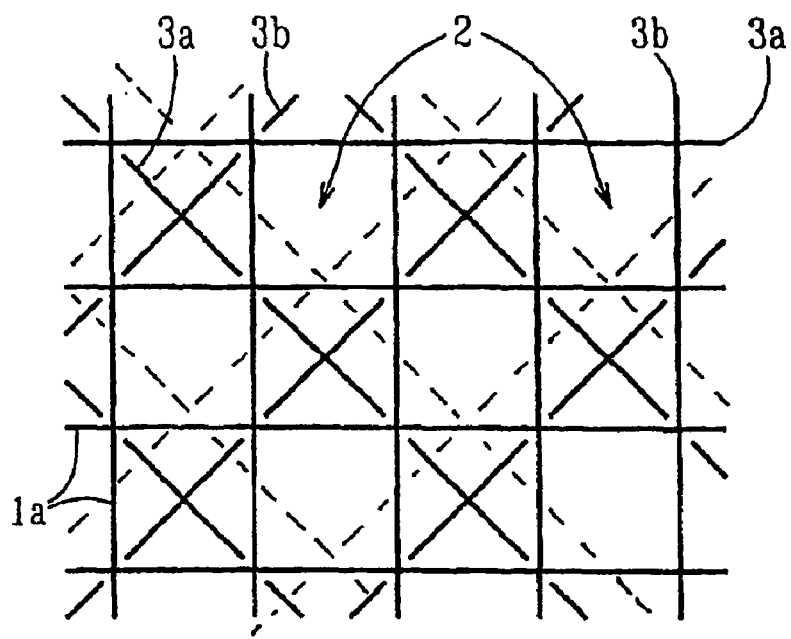
FIG. 7 shows still one example of a piled structure in top plan view.

FIG. 7 shows textile structures piled crosswise as seen in the z-direction. Two fabric layers 1a and 1b on top of each other have openings 2 of different sizes, and the fabric with a larger opening size is at a 45 degree angle. This is an example that the woven fabrics need not have identical spacings between the yarns and that the yarns need not run in parallel relationship in successive layers 1a, 1b. Although it is shown here that the weft and warp yarns 3a, 3b of the lower fabric run through the crossings of the weft and warp yarns of the upper fabric and cover with their crossings every other smaller opening of the upper fabric, the positioning of the openings 2 may be quite random, as denoted with broken lines.

The porosity of the structure can be determined by the textile structures, especially how large openings are left between the yarns in the textile structure and what-will they sizes be after the final pressing stage. The final structure may have average pore size of about 300 to 1000 µm, as measured along the xy plane of the layers, the size being sufficient for transport of a wide variety of bioactive agents and cells, but it can be smaller, starting from 10-20 µm, which still allows the diffusion of some chemical or biological substances.

For obtaining good strength, the content of the reinforcing fibers in the final product should be more than 10 vol-%, an optimal content being 50 to 60 vol-%.

Several layers piled on top of each other need not be constituted of materially different pieces. They can be made also by folding different sections of one and the same blank instead of forming the layers of separate pieces. Likewise, the same blank can be rolled around itself, in which case the different layers are formed of concentric successive laps of the same blank. In this case, when a cylindrical body is taken as a simple example, one of the two dimensions x,y would run in peripheral direction and the other in axial direction, the third dimension z extending through the cylinder radially. These structures can be stiffened to their final shape by the same methods that can be used for structures piled from materially separate pieces of textile.

The structure in its simplest form is planar, that is, it has a general plane parallel with the xy-planes of the textile layers, formed of layers of approximately the same dimensions in the xy-plane. However, the layers may be of different sizes and shapes, in which case more complicated structures can be achieved by suitable selection of the shapes and sizes of the individual consecutive layers.

If the layers are permanently fixed to each other, e.g. by using the properties of the thermoplastic bioabsorbable matrix polymer, certain deformability (e.g. by bending) may still exist in the structure, depending on the dimensions and the textile structure. However, its is possible that the layers are not fixed in fixed positions with respect to their xy-plane, but at least some mobility between the layers is allowed along these planes, which results in complete shapeability of the structure. Of course, structures that are stiff and practically non-deformable at the moment of placing them on the implantation site are preferred for the load bearing (torsion, bending and tension) medical devices used for the osteochondral (hard tissue) applications.

Finally, the porosity of the structure described above can be open, partly open or closed (pores filled partly or completely with material). The pores can be filled completely or partly by a suitable material in the form of powder, non-woven, solution or melt. The material has preferably some bioactive function in the medical device. If the added material is prone to becoming diffused out of the structure through the pores, a bioabsorbable polymer film, which will degrade later in the living body, may be laid over the surface of the porous structure to prevent the diffusion before the implantation. The added material can be synthetic (polymer powder, ceramic powder) or natural (bone graft in powder form, or protein, such as collagen, or polysaccharide or its derivative, such as chitosan). The following section also mentions some materials that can be present in the pores.

Other Materials

Other materials, especially bioactive materials, may be incorporated in the structure, in the pores or in the matrix material or in both. Matrix material may contain other material than the pores do. The site of the material depends on the desired function, rate of release and processability (e.g. thermal resistance if the material is to be incorporated in the bioabsorbable matrix polymer by melt processing). Bioactive agents, e.g. cytokines and/or pharmaceutical agents, may be impregnated in the porous structure of the medical device or may be embedded in the matrix polymer of the structure. Furthermore, living cells, e.g., genetically modified or non-modified, can be incorporated in the structure according to need and clinical indication for the treatment of specific problems, especially those of the skeleton occurring in body of mammals following congenital or acquired tissue defects or discontinuities. They can be impregnated or seeded in the porous structure of the medical device, and consequently living cells can attach, survive, receive nutrients, get rid of waste products, maintain their phenotype and synthesize appropriate extracellular matrix, in acceptable fashion that will lead to tissue generation (tissue engineering), regeneration, repair or proper augmentation of wound or defect healing and tissue formation in the clinical end-applications. Especially the hybrid medical device of the current invention with the living cells can be used to enhance and/or support generation, regeneration, repair or augmentation of tissues and/or defect healing, e.g., fractures or osteotomies or cartilage or bone defects.

Cytokines, such as appropriate growth factors (e.g., BMPs, angiogenic factors etc.) and/or pharmaceutical agents, agents used for diagnosis or indicators for follow up of treatment and integratioin, and/or genes/gene vectors, natural and synthetic genetic materials or chromosomes, can be carried in the porous structure of the medical device, and consequently bioactive agents are able to exert their effect on the clinical end-applications.

As an alternative to or additionally to the impregnation in the pores, bioactive agents, e.g. pharmaceutical agents (e.g., antimicrobial agents), can be dispersed in the bioabsorbable polymer component of the medical device, and consequently the bioactive agents induce their effect on the clinical end-applications.

Micro-organisms, e.g., therapeutic bacteria strains, possibly preventing or healing inflammation, can be impregnated into porous structure, which can be implanted in the body. In this case antimicrobial agents are not incorporated in the structure.

The bioceramic component may be present in the matrix in addition to the bioactive ceramic material in fiber form. Bioactive ceramic particles, such as calcium phosphates (e.g. hydroxyapatite and/or beta-tricalcium phosphate), can be dispersed by melt-blending methods such as single- or twin-screw extruder processing or by solution-blending methods such as solvent processing or subsequent solvent evaporation in the bioabsorbable polymer component of the medical device, an consequently, the bioactive ceramic particles induce their effect on the medical end-applications. It is possible that the fibrous elements 3 contain bioactive glass fibers as reinforcement for the bioabsorbable polymer matrix and other ceramic component, especially one or several calcium phosphates, e.g. hydroxyapatite and/or beta-tricalcium phosphate, dispersed in the same bioabsorbable polymer matrix.

The bioactive agents or living cells can be impregnated into porous structure so that they exist together with bioactive agents such as pharmaceutical agents dispersed in the bioabsorbable polymer component of the medical device, and consequently, both components induce their combined effect on the medical end-applications. Especially the bioactive agents or living cells impregnated or seeded into porous structure together with bioactive ceramic particles, such as hydroxyapatite and/or beta-tricalcium phosphate, dispersed in the bioabsorbable polymer component of the medical device, induce their combined effect on the medical end-applications.

Bioactive agents, e.g. cytokines and/or pharmaceutical agents, can be dispersed in the bioabsorbable polymer component of the medical device together with bioactive agents, such as pharmaceutical agents and with bioactive ceramic particles, such as hydroxyapatite and/or b-tricalcium phosphate dispersed in the bioabsorbable polymer component of the medical device, and they consequently induce their combined effect on the medical end-applications.

In case of bone repair and healing (fixation, regeneration/generation, augmentation) clinical end applications, an example of an important bioactive agent is anti-osteolytic agent that inhibit bone resorption, such as agents that interfere with inflammation or agents that inhibit osteoclasts (anti-osteoclastic), can be included in the matrix of the device of the current invention. An important example of this group of agents belongs to a group called bisphosphonates (see also Watts WB:Bisphosphonates therapy for postmenopausal osteoporosis. South Med J. 1992;85(Suppl):2-31.).

Alternatively or additionally, the bisphosphonate can be impregnated in the pores and/or outer surface of the medical device.

b) Osteoconductive Material

The osteoconductive material that is used in the implant device can be any factor known to create a favorable environment for new bone growth, most commonly by providing a scaffold for bone ingrowth. The osteoconductive factors that can be used is the extracellular matrix protein, collagen. Examples of other important osteoconductive factors are also the bioceramic materials hydroxyapatite (HA), beta-tricalcium phosphate (beta-TCP), bioactive glass), which are already discussed above, and bone grafts (autogenic, allogenic or xenogenic bone grafts) or their derivatives or composites. Two or more of the above-mentioned factors can be used in combination. The osteoconductive factors HA, beta-TCP and/or BaG can be embedded in the matrix polymer, preferably so that they are exposed in the pores at zero time point or after the degradation of the polymer uncovering them gradually (e.g. during the period of 1-3 months) and exposing them to be accessed by surrounding cells and tissues. In case of other materials, such as collagen, they can be used in the pores and the channels of the structure of the device of the present invention. Thus, collagen, fibronectin, etc. can be used as coating in the pores to enhance cell attachment.

c) Osteoinductive Material

The osteoinductive material that is used in the implant device can be any osteoinductive protein that is known to stimulate new bone production. These proteins include PDGF, IGF-I, IGF-II, FGF, TGF-beta and associated family members. The most effective bone formation-inducing factors are the bone morphogenetic proteins (BMPs). Angiogenic factors such as VEGF, PDGF, FGF etc. can also be incorporated to enhance/maintain bone formation process where suitable. Two or more of the above-mentioned factors can be used in combination.

Applications

The structure can have a wide variety of applications especially in osteochondral medical devices. It is designed to be implanted in a living mammalian body. The bioactive and bioabsorbable composite medical device structure can be implanted into human body to induce and/or enhance and/or support hard tissue generation, regeneration, repair or augmentation. Bioactive ceramic reinforcing component of the composite medical device can be used for fixation of the implant in host tissue. The device of the current invention can be used either alone or in combination with other methods such as fixation with bioabsorbable or metallic screws, tacks, bolts, plates, sutures, etc. Accordingly, the porous, bioactive and bioabsorbable medical device structure can be used for tissue repair (e.g., bone fixation), regeneration (e.g., guided bone regeneration) or for tissue generation (e.g., tissue engineering) or augmentation.

Figure 8:
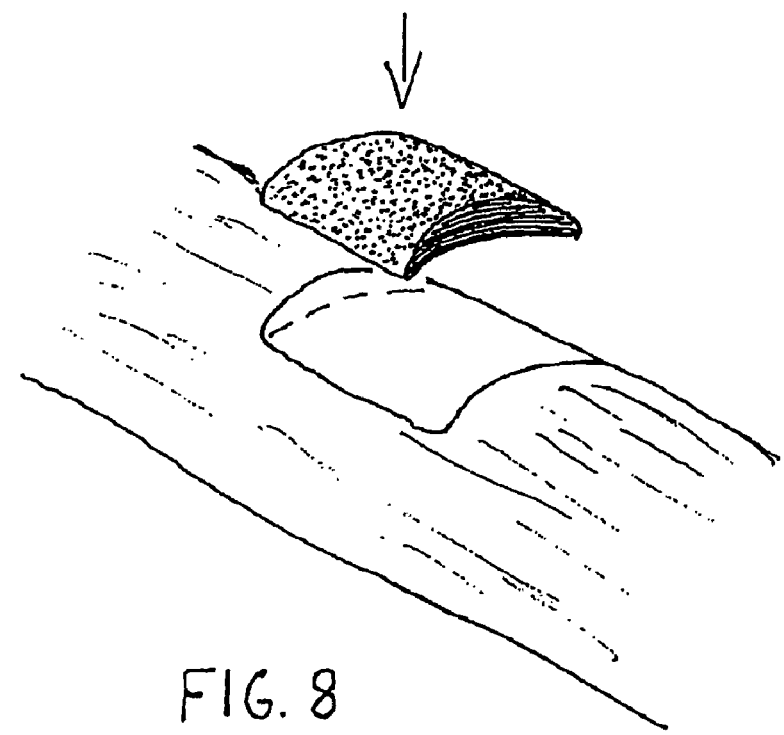
FIG. 8 shows one example of a possible orthopaedic application.

FIG. 8 shows schematically an example of the application in bone repair, where the structure of the medical device has been shaped to a suitable form before it is placed to fill a defect in the bone.

Once implanted in the body, the bioactive ceramic element component of the device of the current invention, is arranged in a way to induce tissue growth and confer primarily mechanical properties (e.g. strength and moduli) and the bioabsorbable polymer matrix component is arranged in a way to simultaneously induce adhesion between the reinforcing bioactive components and transfer the external load to these components, and partially confer mechanical properties, to provide a composite for tissue fixation or support.

The degradation rate of bioabsorbable composite structurecan be adjusted according to the requirements imposed by the clinical end-applications, inducing different durational strength retention fixation periods encountering the application healing needed.

The rate of the chemical reaction of bioactive ceramic fibers can be adjusted according to the requirements needed for clinical end-applications inducing different time periods for tissue growth encountering the application.

Porous structure in the device of the current invention is continuous throughout the structure, i.e. pores form interconnecting porosity inside the medical device composite structure. This allows the continuous transportation of organic substances, living cells (genetically modified or non-modified, autogenic or allogenic) and biologically active agents (e.g., cytokines and/or pharmaceutical agents), and inorganic ions inside medical device composite structure. The multi-functionality of the medical device is possible to achieve because of integration of a bioactive agent component in the pore site and/or dispersion of the biologically active agent component into the polymer matrix. The choice is dependent on the desired controlled release rate of the agent. If the structure is in planar configuration having constant thickness proportional to the number of piled textile layers, the originally planar structure can be formed with the aid of heat and pressure or only mechanically forming (i.e., manual bending at room temperature) into specific 3-D shaped structures.

Before or at the time of application in the surgical theatre, the surgeon himself/herself can shape the device to a desired 2-D or 3-D form according to the patients requirement, starting from a blank of several textile layers by using molding techniques (e.g. heat and pressure).

Thus, it is possible to make a final porous piece which is load-bearing and stiff and where the deformation is reversible after the load (for example bending) to which the structure is subjected is removed.

EXAMPLE OF AN EMBODIMENT
(NON-LIMITING)

Starting materials were continuous monofilament of bioabsorbable PLLA made by fiber spinning with a diameter about 200-300 μm and bioactive glass made by spinning with a diameter 20-30 μm. These filaments were knitted together by a flat-bed knitting machine Stoll UFD with an interlock setting. Pieces of 300×300 mm were cut from the knit and four of them were piled on top of each other so that the orientations of the different layers in the machine direction coincided. The melting point of the matrix polymer used being 180° C., the laminate blank was compression moulded into a porous cellular plate at a temperature of 110-130° C., which was the range set for the machine. At the processing stage, a set of temperature and pressure (100-150 kN) profiles as a function of time was followed. Finally, the piece was air cooled under a weight of 30 kg. The thickness of the laminate was about 6 mm and the density with pores was 500 kg/m3, Samples of the cellular plate were sawn for bending test.

Figure 9:
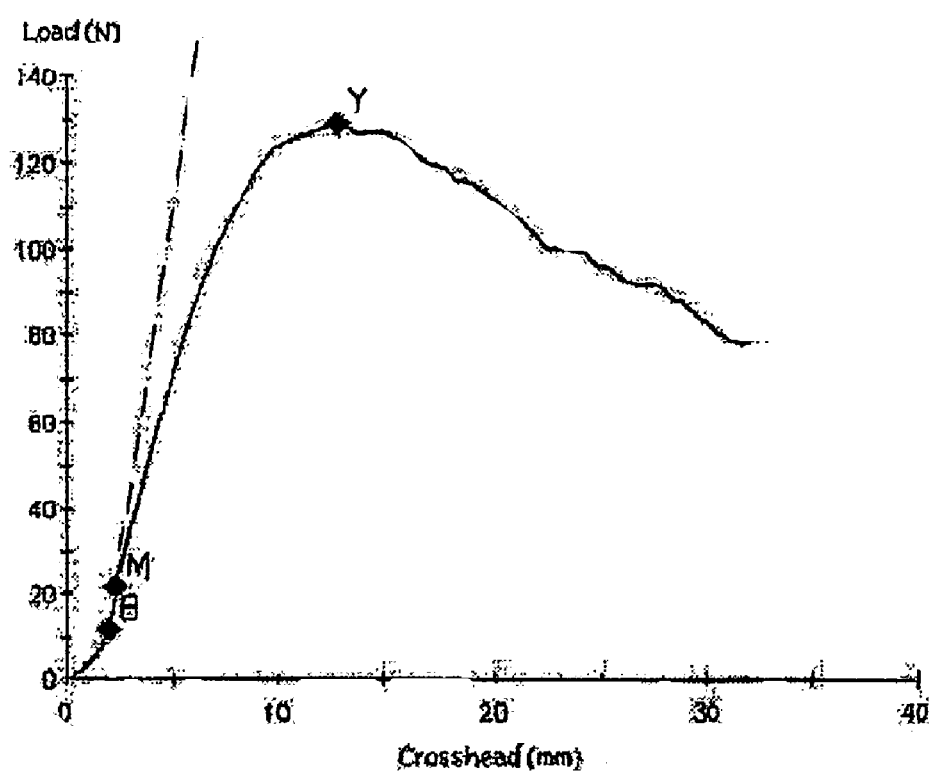
FIG. 9 shows a curve of a bending test.

FIG. 9. shows the result of a bending test of the aforementioned porous, load-bearing bioabsorbable sample composed of melted biopolymer filament matrix and bioactive reinforcement glass filament. A straight sample was supported at both ends and pressed down in the middle by a crosshead with measured forces and extensions. The curve obtained is typical for stiff pieces having an elastic region.

The invention claimed is:

1. A porous bioabsorbable, bioactive and load-bearing medical device composite structure having a bioabsorbable matrix and reinforcing structure, said composite structure further comprising:
    a plurality of textile planar layers, said layers being formed of continuous fibrous elements and being placed on top of each other to a position with respect to each other to form a structure having two dimensions which are non-parallel to each other and a third dimension originating from piling of said planar layers on top of each other;
    a plurality of openings extending through said layers, said openings being defined by portions of said continuous fibrous elements extending substantially in the direction of said plane and existing in the textile planar layers prior to placing them on top of each other;
    a plurality of passages extending through said structure, said passages being formed of the openings in different textile planar layers placed on top of each other;
    a reinforcing structure formed by reinforcing bioactive ceramic fibers included in said continuous fibrous elements; and
    a bioabsorbable matrix formed by bioabsorbable polymer matrix material also included in said continuous fibrous elements;
    the position of the layers with respect to each other being fixed when said bioabsorbable polymer matrix binds together said portions of said continuous fibrous elements defining said openings and binds said layers together, simultaneously stiffening said structure;
    said bioabsorbable polymer matrix material comprising bioabsorbable thermoplastic polymer material or polymer blend material, and said continuous fibrous elements defining said openings are bound together and the structure is stiffened by said bioabsorbable thermoplastic polymer material or polymer blend material softened or melted in heat treatment and solidified.

2. A structure according to claim 1, wherein said textile planar layers are regular textile planar layers whose openings make the planar layers regular in structure.

3. A structure according to claim 2, wherein the regular planar textile layers are selected from the group consisting of knitted, woven, and braided layers.

4. A structure according to claim 3, wherein said regular textile planar layers comprise knitted layers, said passages being formed by loops in different layers of said knitted layers.

5. A structure according to claim 3, wherein said regular textile planar layers comprise woven layers including weft and warp yarns; and said passages are formed by openings between said weft and warp yarns.

6. A structure according to claim 2, wherein the structure comprises two or several textile planar layers of different types, selected from the group consisting of knitted, woven or braided layers, or the structure comprises a commingled layered textile structure of reinforcing bioactive ceramic fibers and bioabsorbable polymer matrix.

7. A structure according to claim 1, wherein the reinforcing bioactive ceramic fibers are filaments.

8. A structure according to claim 1, wherein the continuous fibrous elements are hybrid yarns comprising both reinforcing bioactive ceramic fibers and bioabsorbable polymer matrix.

9. A structure according to claim 1, wherein said continuous fibrous elements comprise a continuous bioabsorbable polymer matrix filament and reinforcing bioactive ceramic filament.

10. A structure according to claim 1, wherein said continuous fibrous elements comprise a reinforcing bioactive ceramic filament and a bioabsorbable polymer matrix coating on it.

11. A structure according to claim 8, wherein said continuous fibrous elements comprise reinforcing bioactive ceramic staple fibers and bioabsorbable polymer matrix staple fibers spun together.

12. A structure according to claim 1, wherein said bioactive ceramic fibers are bioactive glass or calcium phosphates.

13. A structure according to claim 1, wherein the bioactive ceramic fiber component is arranged to induce tissue growth and the bioabsorbable polymer matrix component is arranged to simultaneously induce fixation or support strength in an implanted medical device.

14. A method of manufacturing the porous bioabsorbable, bioactive and load-bearing composite medical device of claim 1, the method comprising: providing a plurality of textile planar layers, said layers being formed of continuous fibrous elements and having each a plurality of openings defined by portions of said continuous fibrous elements, said fibrous elements comprising a bioabsorbable matrix formed by bioabsorbable polymer matrix material and reinforcing ceramic elements;
placing said textile planar layers on top of each other to form a piled structure having two dimensions at right angles to each other and a third dimension perpendicular to them and originating from piling of said textile layers on top of each other, the piled structure having passages extending through said structure and formed of the openings in different textile planar layers.

15. A method according to claim 14 wherein the method further comprises fixing the layers to each other.

16. A method according to claim 15, wherein the layers are fixed by heat.

17. A method according to claim 16, wherein said bioabsorbable polymer matrix material is thermoplastic bioabsorbable polymer matrix material, and the layers are fixed by means of said thermoplastic bioabsorbable polymer matrix material by subjecting it to heat and then cooling.

18. A method of using the structure of claim 1 as a bioabsorbable, bioactive and load-bearing composite medical device or part thereof in desired shape in hard tissue repair, augmentation or regeneration, or in hard tissue generation.

19. A structure according to claim 1, wherein bioactive agents selected from a group consisting of cytokines and pharmaceutical agents, and/or living cells and/or micro-organisms are incorporated in the structure.

20. A structure according to claim 19, wherein genetically modified or non-modified living cells are impregnated or seeded in the pores of the structure.

21. A structure according to claim 19, wherein both bioactive agents selected from a group consisting of cytokines, appropriate growth factors, BMPs, angiogenic factors, pharmaceutical agents, genes, gene vectors, natural and synthetic genetic materials and chromosomes, are carried in the pores of the structure, and genetically modified or non-modified living cells are seeded in the pores of the structure.

22. A structure according to claim 19, wherein the bioactive agents selected from the group consisting of cytokines and pharmaceutical agents are dispersed in the bioabsorbable polymer component of the medical device.

23. A structure according to claim 19, wherein bioactive ceramic particles are dispersed in the bioabsorbable polymer component of the structure.

24. A structure according to claim 23, wherein the bioactive ceramic particles are selected from calcium phosphates.

25. A structure according to claim 19, wherein the bioactive agents or living cells are impregnated into the pores of the structure and the pharmaceutical agents are dispersed in the bioabsorbable polymer component of the structure.

26. A structure according to claim 19, wherein micro-organisms capable of preventing or healing inflammation and/or bioactive agents are impregnated into the pores of the structure.

27. A structure according to claim 23, wherein the bioactive agents or living cells are impregnated into the pores of the structure and the bioactive ceramic particles are dispersed in the bioabsorbable polymer component of the structure.

28. A structure according to claim 23, wherein the bioactive agents are dispersed in the bioabsorbable polymer component of the structure and the bioactive ceramic particles are dispersed in the bioabsorbable polymer component of the structure.

* * * * *